(12) United States Patent
Cooke

(10) Patent No.: US 9,030,673 B2
(45) Date of Patent: May 12, 2015

(54) CIRCUMFERENTIAL LASER CRAWLER

(75) Inventor: Barry Theophile Cooke, Black Diamond, WA (US)

(73) Assignee: The Boeing Company, Chicago, IL (US)

( * ) Notice: Subject to any disclaimer, the term of this patent is extended or adjusted under 35 U.S.C. 154(b) by 128 days.

(21) Appl. No.: 13/441,239

(22) Filed: Apr. 6, 2012

(65) Prior Publication Data

US 2013/0265588 A1    Oct. 10, 2013

(51) Int. Cl.
| | |
|---|---|
| *G01B 11/24* | (2006.01) |
| *G01S 17/66* | (2006.01) |
| *G01N 21/95* | (2006.01) |
| *B64F 5/00* | (2006.01) |
| *G01S 7/481* | (2006.01) |
| *G01C 15/00* | (2006.01) |

(52) U.S. Cl.
CPC ............. *G01B 11/24* (2013.01); *G01S 17/66* (2013.01); *G01N 21/9515* (2013.01); *B64F 5/0045* (2013.01); *G01S 7/481* (2013.01); *B64F 5/0009* (2013.01); *G01C 15/002* (2013.01); *G01N 2291/2694* (2013.01); *G01N 2021/9518* (2013.01)

(58) Field of Classification Search
None
See application file for complete search history.

(56) References Cited

U.S. PATENT DOCUMENTS

| | | | |
|---|---|---|---|
| 5,633,707 A | 5/1997 | Seemann | |
| 7,155,307 B2 * | 12/2006 | Seemann | 700/245 |
| 7,743,660 B2 | 6/2010 | Marsh | |
| 7,978,322 B2 * | 7/2011 | Marsh et al. | 356/152.1 |
| 2005/0132811 A1 * | 6/2005 | Mueller | 73/620 |
| 2008/0030855 A1 | 2/2008 | Lau | |
| 2012/0320372 A1 * | 12/2012 | Troy et al. | 356/237.2 |

FOREIGN PATENT DOCUMENTS

JP          2000162307 A        6/2000

OTHER PUBLICATIONS

Liu, et al."Design and CAD-directed inspection planning of laser-guided measuring robot", Computers and Graphics, Elsevier, GB, vol. 32, No. 6, Dec. 1, 2008, pp. 617-623.
European Search Report Application No. EP13161740 dated May 9, 2014.

* cited by examiner

*Primary Examiner* — Kara E Geisel
*Assistant Examiner* — Amanda Merlino
(74) *Attorney, Agent, or Firm* — Kunzler Law Group, PC

(57) ABSTRACT

An automated motorized assembly may be utilized to move a laser reflector on inside or outside surfaces, along edges of barrel shape structures. The laser reflector may be used to reflect laser signals back to a laser tracker metrology system locked in on the laser reflector. The laser tracker may follow the laser reflector as it moves along an edge of a barrel shape structure, acquiring circumferential data. The laser reflector may be moved to different positions to enable obtaining different circumferential rows of data. The automated motorized assembly may comprise a movement component that ensures consistent, continued, and/or tight movement along the traversed edge. The movement component may comprise a plurality of wheels and/or rollers, and one or more motors for driving at least some of the wheels and/or rollers. The automated motorized assembly may be controlled by user input, which may be communicated wirelessly.

19 Claims, 9 Drawing Sheets

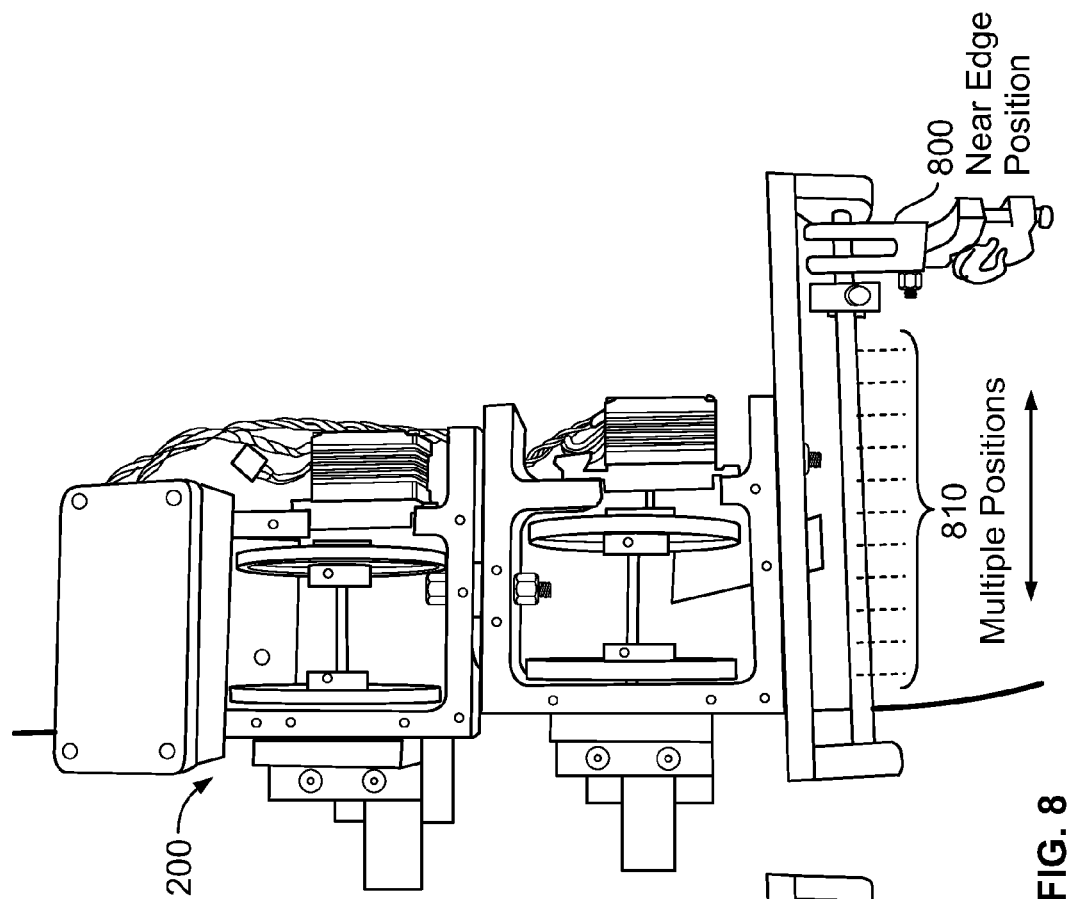
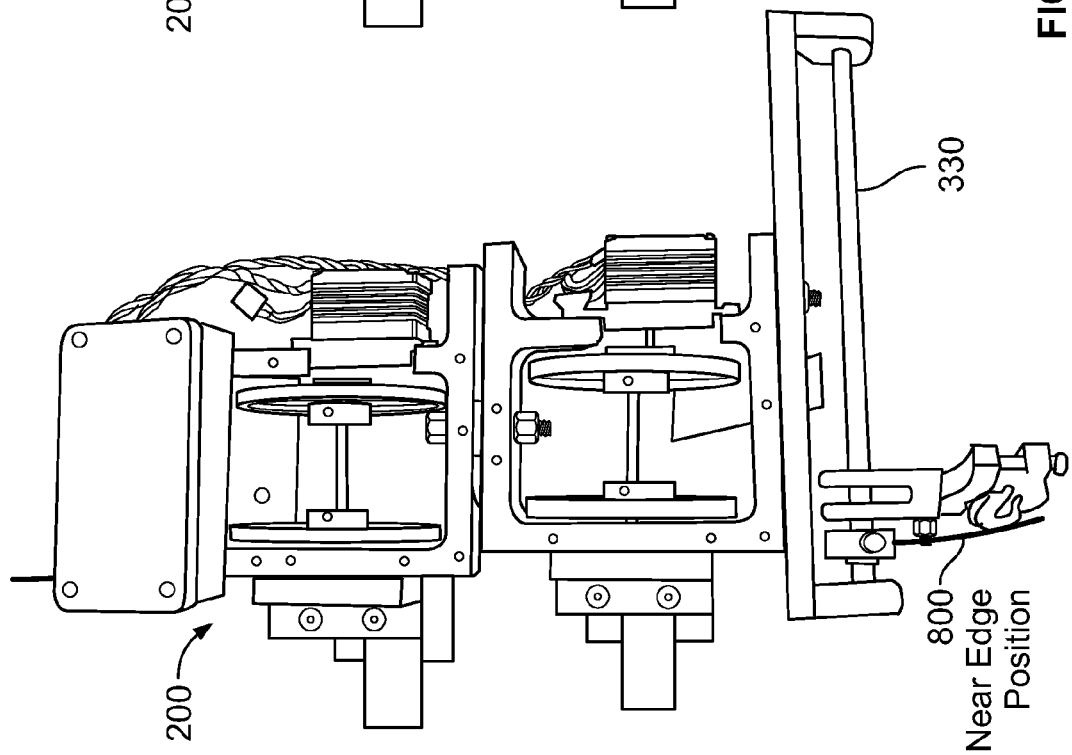
FIG. 8

CIRCUMFERENTIAL LASER CRAWLER

CLAIM OF PRIORITY

[Not Applicable]

CROSS-REFERENCE TO RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable].

FIELD

Certain embodiments of the invention relate to manufacturing and more specifically to measurement related operations during manufacturing. More specifically, certain embodiments of the invention relate to an apparatus and method for a circumferential laser crawler.

BACKGROUND

Manufacturers are under continual pressure to reduce costs associated with and/or enhance efficiency of manufacturing processes. In this regard, manufacturing a particular article (e.g., airplane) may require performing various steps to produce a complete example of the article. The type of steps undertaken in a manufacturing process may be dictated by the article itself and/or by other conditions pertinent to the manufacturing process (e.g., use of sub-contractors for producing components of the article). For example, manufacturing airplanes may require assembling components, such as fuselage sections, which may be made separately, sometimes by different sub-contractors and/or at different locations. Accordingly, the manufacturing process may comprise performing various measurement steps, such as to ensure that the different fuselage sections match during the assembly of airplanes. One type of measurement typically performed during assembly of airplanes is circumferential measurement, which is directed at obtaining measurements relating to the circumference of cylindrical or rounded shaped structures, such as fuselage sections. Current methods for performing circumferential measurement are typically based on radar metrology techniques, which tend to be time consuming and require use of expensive equipment.

Therefore, it would be advantageous to have a circumferential measurement apparatus and method that reduce data collection time and/or cost, while maintaining or even improving accuracy.

Further limitations and disadvantages of conventional and traditional approaches will become apparent to one of skill in the art, through comparison of such systems with some aspects of the present invention as set forth in the remainder of the present application with reference to the drawings.

SUMMARY

An apparatus and/or method is provided for a circumferential laser crawler, substantially as shown in and/or described in connection with at least one of the figures, as set forth more completely in the claims.

In one aspect, an apparatus for measuring circumferential data for barrel-like and/or curvilinear structures may comprise an automated motorized device operable to run along curvilinear shaped edge of a structure. The automated motorized device may comprise a plurality of drive wheels and/or rollers, and a reflector that may be operable to reflect signals back to a source of the signals. The source of the signals may be a laser tracking metrology system. The reflector may be moved to different positions relative to the edge, to enable obtaining different circumferential rows of data.

In another aspect, a method for measuring internal and/or external surface definitions of barrel-like and/or curvilinear structures may comprise positioning a reflector of an automated motorized device in a particular location relative to a curvilinear edge of a structure. The circumferential row of data at the particular location may be obtained and/or generated by moving the automated motorized device along the curvilinear edge, acquiring circumferential coordinate data during movement of the automated motorized device using a laser tracker metrology system, and continuing to move the automated motorized device and acquire circumferential data until a complete circumferential row of data is obtained. A plurality of other circumferential rows of data may be obtained by repositioning the reflector of the automated motorized device in a plurality of other locations, and obtaining a circumferential row of data at each of the plurality of positions.

These and other advantages, aspects and novel features of the present invention, as well as details of an illustrated embodiment thereof, will be more fully understood from the following description and drawings.

The features, functions, and advantages that have been discussed can be achieved independently in various embodiments or may be combined in yet other embodiments further details of which can be seen with reference to the following description and drawings.

BRIEF DESCRIPTION OF THE DRAWINGS

FIG. 8 is a diagram illustrating a reflector traversing component of a circumferential laser crawler for enabling adjustment of positioning of reflector relative to edges, in accordance with an advantageous embodiment of the invention.

DETAILED DESCRIPTION

Certain embodiments of the invention may be found in a method and system for a circumferential laser crawler. Many specific details of certain embodiments of the invention are set forth in the following description as well as the drawings to provide a thorough understanding of such embodiments. One skilled in the art, however, will understand that the present invention may have additional embodiments, or that the present invention may be practiced without several of the details described in the following description. Like numbers refer to like elements throughout.

Laser tracking based measurement may be utilized to obtain circumferential data pertaining to internal and/or external surfaces of curvilinear shaped objects, which may comprise barrel like structures, such as the fuselage sections utilized in assembling airplanes. In this regard, an automated motorized device, which may be operable to tightly traverse along curvilinear shaped edges, may be utilized to move a laser reflector, which may be attached to the automated motorized device, along the edge of a structure being measured. A laser tracker may be locked on the laser reflector following its movement along the edge as the automated motorized device traverses the edge, thus acquiring circumferential data, until a complete acquiring circumferential row of data is obtained—e.g., by completing a full run along the edge. Additional circumferential rows of data may be obtained by repositioning the laser reflector to different positions relative to the traversed edge, and repeating the process until a corresponding, complete circumferential row of data is obtained. The automated motorized device may comprise a movement component that is configured to enable tight and/or secure traversing along curvilinear edges. The automated motorized device may comprise, for example, a plurality of drive wheels and/or roller.

Figure 1:
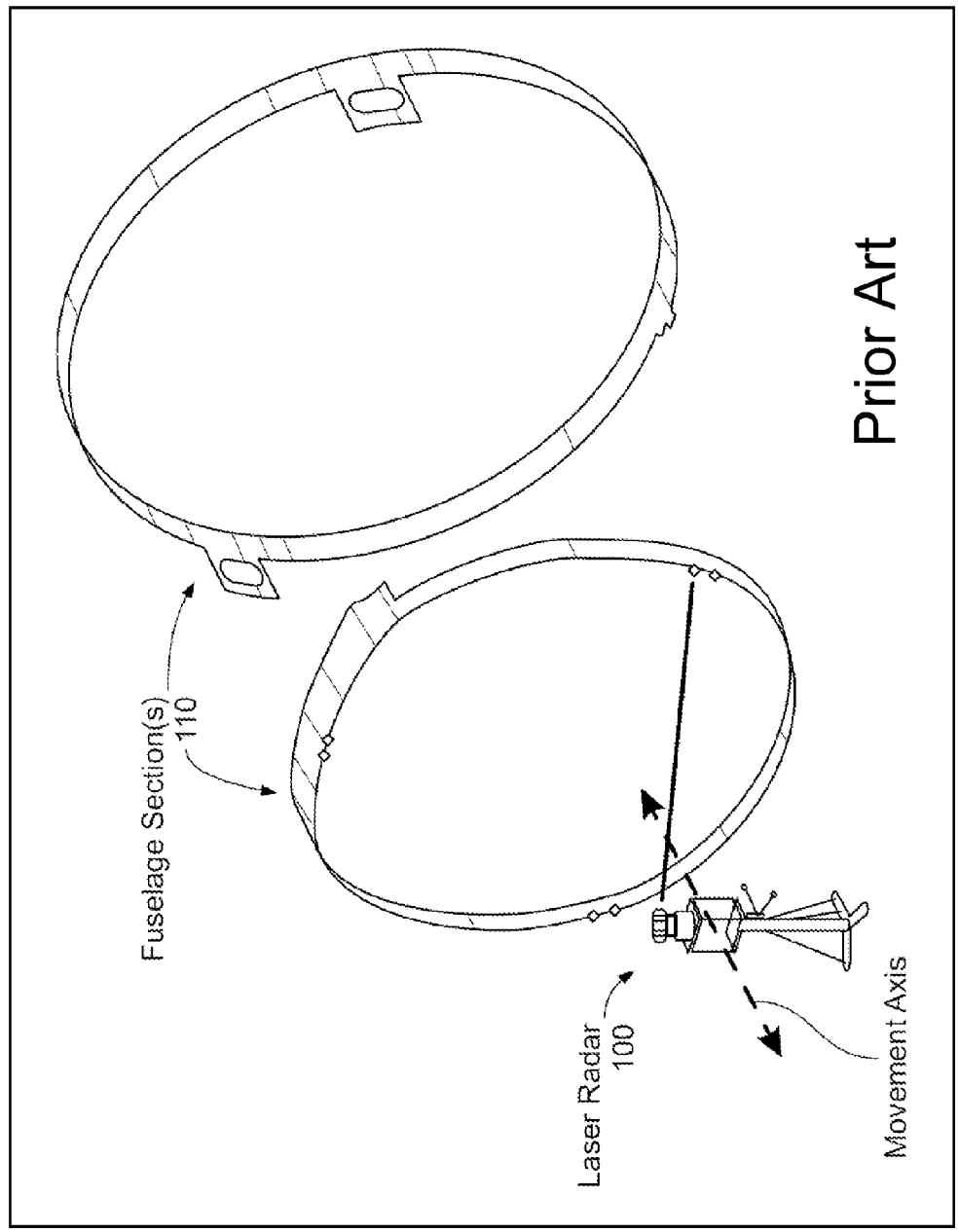
FIG. 1 is a diagram illustrating use of laser radar for providing circumferential measurements.

FIG. 1 is a diagram illustrating the use of laser radar for providing circumferential measurements. Referring to FIG. 1, there is shown a laser radar 100 and fuselage sections 110.

The laser radar 100 may be utilized to perform measurements, in particular circumferential measurements of curvilinear shaped structures, which may comprise barrel like structures, such as the fuselage sections 110 for example. In this regard, the laser radar 100 may be a computer-aided portable device, which may be used to measure surfaces without requiring physical targets other than the structure whose surface is being measured. In particular, the laser radar 100 may operate by emitting laser beams towards the surface of the structure, and may then perform measurement of the surface in radar-like manner, that is based on processing of signal reflections off the surface that are received back by the laser radar. In other words, the laser radar 100 may perform circumferential measurements based on a plurality of natural surface points, by calculating the horizontal and/or vertical angles of what the laser radar 100 is pointing at and determining the range based on the reflection of the laser off the surface, which also require accounting for variations in the reflection profile as a result of the topology of the surface itself. In this manner, the laser radar 100 may be used to scan circumferential rows of data, wherein each row corresponds to different distance or depth from the edge (rim) of the structure. For example, a first row may correspond to the rim itself, and each successive row thereafter may correspond to a fixed distance increment from the previous row in away from the rim direction. In this regard, the laser radar 100 may be moved forward or aft relative to the barrel-like structure, to measure points that are different depths or levels relative to the edge (rim) of the structure. Alternatively, the laser radar 100 may comprise a moving mechanism that may enable adjusting the scanning angle—e.g., by adjusting the angle to the laser transmitter/receiver component(s). In this regard, the laser radar 100 may be moved forward or aft physically to measure points at different depths from the edge of the structure. Nonetheless, more commonly measurements using laser radars, such as the laser radar 100, may obviate the need for physical movement of the laser radar itself by incorporating other means, such as software applications, to enable configuring the laser radar components to measure at different depths or rows using theoretical points as the defining point to measure.

The use of laser radar 100 in performing circumferential measurement, however, has some disadvantages. For one, laser radars are typically expensive equipment. Also, performing circumferential measurements using laser radar 100 may be time consuming. In this regard, determining the range for each measured point requires a significant amount of time (e.g., few seconds) as a result of the need to process the reflection, to account for any variation caused by the topology of the surface itself for example. Therefore, in order to measure a data row for particular surface, the laser radar 100 may require substantial time to complete the measurement since it has to measure a large number of points (e.g., typically a few hundred points for a fuselage section), and reducing the number of measured points, to reduce the measurement time, may be undesirable since doing so may adversely affect the reliability of the measurement—i.e., the less measurement points are used the less reliable the measurement may be. Furthermore, use of laser radars for measurements, in particular circumferential measurements, has some inherent limitations. For example, the use of laser radars typically limits the measurements to internal surfaces—that is because the laser radar 100 can only provide measurements based on reflections off various points from the same point of reference, the laser radar 100 must be positioned and/or moved along axels that run through the interior of the structure (e.g., fuselage section). Another limitation of the laser radar is due to the angle of incidence to the surface being measured. In this regard, with radar based mechanisms, the best and most accurate surface measurement would be for the laser beam to be normal or perpendicular to the surface. As the laser beam starts to deviate from the normal condition, however, the measurement uncertainty can increase. Thus if measuring an external barrel-like shape the laser to surface normal condition would change with radial shape of the barrel and the current location of the laser radar system. To accommodate this condition the laser radar 100 would need to be physically moved to another location to provide a better normal condition for the laser beam to continue to measure more surface points. Such need to continually move the laser radar (physically) for external surface points measurements may be a primary cause for the increased time to collect data.

Figure 2:
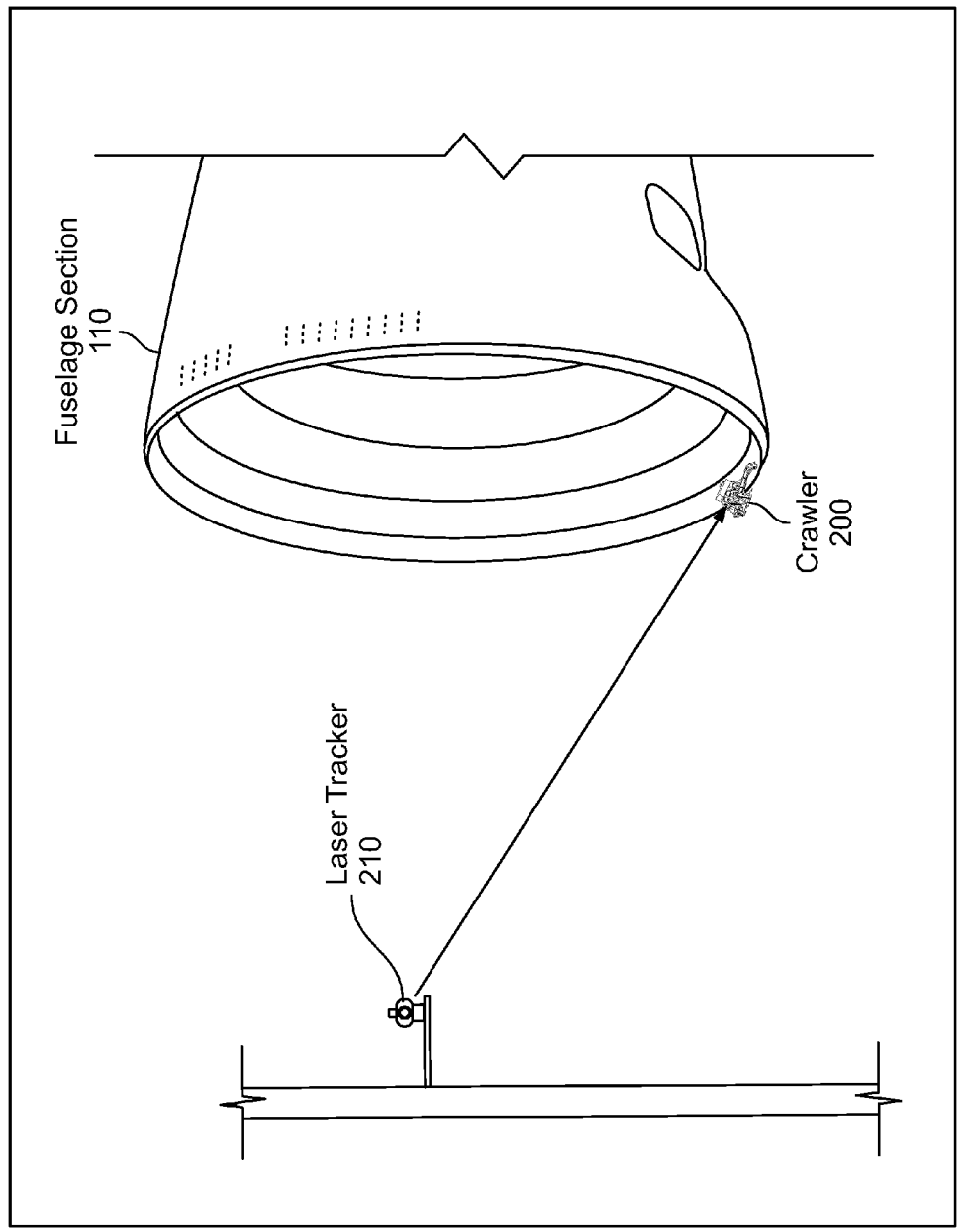
FIG. 2 is a diagram illustrating use of a circumferential laser crawler in conjunction with a laser tracker, in accordance with an advantageous embodiment of the invention.

FIG. 2 is a diagram illustrating use of a circumferential laser crawler with a laser tracker, in accordance with an advantageous embodiment of the invention. Referring to FIG. 2, there is shown the fuselage section 110, a crawler 200, and a laser tracker 210.

The laser tracker 210 may be a computer-aided portable device used to calculate surface related measurement. In this regard, the laser tracker 210 may be similar to the laser radar 100 in that it may determine surface measurement based on reflection of signals, such as laser emitted by the laser tracker 210 itself. Unlike the laser radar 100, however, the laser tracker 210 may perform its calculations, to generate or obtain the surface measurement for example, by tracking the reflection of its signal of a particular physical target that is different from the structure whose surface is being measured. For example, the laser tracker 210 may be configured to lock its laser beam on a particular reflector, which may be suited to reflect a laser beam, having the characteristics of the beam emitted by the laser tracker 210, back to source of the beam. In this regard, the laser beam emitted by the laser tracker 210 reflects off a reflector, and the laser tracker 210 calculates the range based on the time that laser beam may require to travel to that reflector and come back to the laser tracker 210. The laser tracker 210 may remain locked on the reflector. In other words, the measurement by the laser tracker 210 may be performed by simply locking on the reflector, and then following the reflector's movement, such as along the edge of a curvilinear shaped structure like the fuselage section 110 for example, thus enabling calculation of a row of circumferential data by having the reflector complete a turn on the edge.

The crawler 200 may be a portable automated motorized device which may be operable to move a physical target, such as a laser reflector, in a controlled manner to assist the laser tracker 210 in performing surface measurement. In this regard, the crawler 200 may be configured to maintain the laser reflector in a particular position, and may enable moving the reflector in that position along the edge of an structure, such as the fuselage section 110, to enable the laser tracker 210 to generate and/or obtain surface measurement (e.g., circumferential measurement).

The crawler 200 may comprise a plurality of components performing various operations in support of intended functions of the crawler 200. For example, the crawler 200 may comprise a reflector holder component, for providing the necessary function pertaining to the reflector—e.g., holding the reflector at particular position, maintaining the reflector in contact with the surface, etc. The crawler 200 may also comprise a movement component which may enable the crawler 200 to move along an edge of a structure, including curvilinear shaped structures such as the fuselage section 110. In this regard, the movement component of the crawler 200 may be configured to enable the crawler 200 to run on the inside or the outside of the fuselage section 110 or other similar barrel-shaped structures. To that end, the crawler 200 may comprise a clamping component and/or functions to ensure that the crawler 200 grips securely and/or tightly on the traversed edge, and/or that the crawler moved in consistent manner—that is ensuring that the reflector in maintained in the preselected position relative to the edge.

The crawler 200 may also comprise a controller component for controlling various operations and/or components of the crawler 200. In this regard, the controller component may comprise a programmable circuitry providing control signals to at least some of the components of the crawler 200, to enable configuring these components to perform various operations in support of the functions of the crawler 200. For example, the controller component may control operations of the movement component of the crawler 200.

In an embodiment of the invention, the crawler 200 may be configured to receive and/or transmit information, such as by incorporating a communication component for providing and/or handling communications to and/or from the crawler 200. In this regard, the crawler 200 may receive, for example, user input, which may be used in controlling and/or adjusting various operations or functions of the crawler 200. For example, the user input may comprise movement related commands, such as "start" or "stop" and/or other similar commands. The crawler 200 may also be operable to transmit status information, such as information relating to various components or functions of the crawler. The status information may be transmitted to the laser tracker 210 and/or to other devices that may be utilized by users (e.g., computer). The reception and/or transmission may be performed wirelessly, using one or more appropriate technologies. For example, communications may be via infra-red (IR) signals, Bluetooth signals, and/or WiFi signals. The invention is not limited, however, to any particular communication technology.

The laser tracker 210 may be used in conjunction with the crawler 200 in performing circumferential measurement. In this regard, the laser tracker 210 may generate and/or obtain circumferential measurement based on range calculations using laser beams that are directed to the reflector of the crawler, by utilizing timing and/or distance information derived based on reception of reflections back from the laser reflector of the crawler. The reflector of the crawler 200 may be initially set at a particular position, relative to the edge of the fuselage section 110, and the laser tracker 210 may be locked on the reflector—that is the laser tracker 210 may be setup to direct its laser beam at the reflector. The crawler 200 may then move along the edge of the fuselage section 110, with the laser tracker 210 remaining locked on the reflector and following its movement (along with the crawler 200), and this tracking of the reflector may be utilized to enable the laser tracker to generate and/or obtain circumferential measurement for a row corresponding to the reflector position. The process may be repeated with the reflector being moved to different positions, such as by incorporating a sliding component for example which may be combined with or attached to the reflector holder component, thus enabling generating and/or obtaining circumferential measurements for different rows.

Use of the laser tracker 210 in conjunction with the crawler 200 to perform circumferential measurement may provide numerous advantages over other methods, such as radar metrology based techniques (e.g., when using the laser radar 100). Tracking based devices or systems, such as the laser tracker 210 may be significantly cheaper compared to laser radars, and therefore laser tracking based methods may be significantly cheaper than radar based methods, even with the added cost of other devices whose use may be required in tracking based operations—e.g., the crawler 200. In addition, use of laser tracking techniques may result in substantial reduction in time because tracking based range calculations may be many times faster than radar based calculations, since laser trackers utilized reflections from an optimal and already locked on target (e.g., the laser reflector of the crawler 200), thus obviating the need for the complex processing typically required with radar based operations. Also, unlike radar based techniques, which are typically limited to providing circumferential measurements of internal surfaces of barrel-like (or similarly shaped) structures, tracking based measurements in accordance with the present invention may enable generating and/or obtaining circumferential measurements for internal and external surfaces of a structure like as the fuselage section 110. For example, circumferential measurements for external surfaces may be obtained by setting the crawler 200 to move with the laser reflector being positioned directly on (or relative to) the external surface. In this regard, to ensure that the laser reflector remain seen by the laser tracker 210, the laser reflector may be positioned slightly off the external surface, using a predetermined offset from the surface for example, to ensure that the laser reflector is not blocked by the structure at any point during the traversal of the edge, with the laser tracker 210 being configured to account for that offset when generating the measurement for the external surface. To enable and/or accommodate for positioning the laser reflector off of the measured surface—i.e., without direct contact between the laser reflector and the measured surface—a physical component, such as holder mechanism may be incorporated into the crawler 200, which may ensure that the laser reflector may be maintained at particular and constant offset as the crawler 200 traversed the measured surface. Furthermore, to guard against errors resulting for such positioning offset, the measurement calculations may be configured to account for that offset. For example, the laser tracker 210 may be informed of the positioning offset between the laser reflector and the measured surface, being applied via the laser reflector holding component, and the laser tracker 210 may then incorporate and/or account for that offset when calculating the circumferential measurements.

The tracking based approach may also result in enhanced reliability compared to radar based techniques. The use of the crawler 200 to move the laser reflector that the laser tracker 210 is locked on, along the edge of the structure being measured, may enable increasing the number of measurement points read when obtaining circumferential measurement for a particular row. In this regard, because the added complexity required for processing unpredictable signal reflections, laser radar based methods may only allow measuring limited number of points—e.g., every one inch or half inch, to minimize the amount of time it takes to obtain circumferential measurement for a row. On the other hand, because handling the signal reflections and performing the calculations based thereon (and thus the measurements) are done much faster with laser trackers, the use of the combination of the laser tracker 210 and the crawler 200 may enable capturing measurement data at much higher rate, in time and/or distance. The laser tracker 210 may, for example, obtain measurement related readings in as small as a fraction of a second and/or at very small spatial intervals (e.g., every tenth). In other words, because the laser tracker 210 remains locked on the laser reflector attached to the crawler 200 as it moves along the edge, data may be collected at any rate, thus allowing for collection of substantial amount of data, much more than typically possible with radar based techniques, while still being able to do so in timely manner (e.g., even in less time). One other advantage is the ability to control and/or adjust the measurement operations by adjusting the crawler 200 and/or its movement using the communication link available with the crawler 200, which may allow for very flexible data collections and/or measurement.

Figure 3:
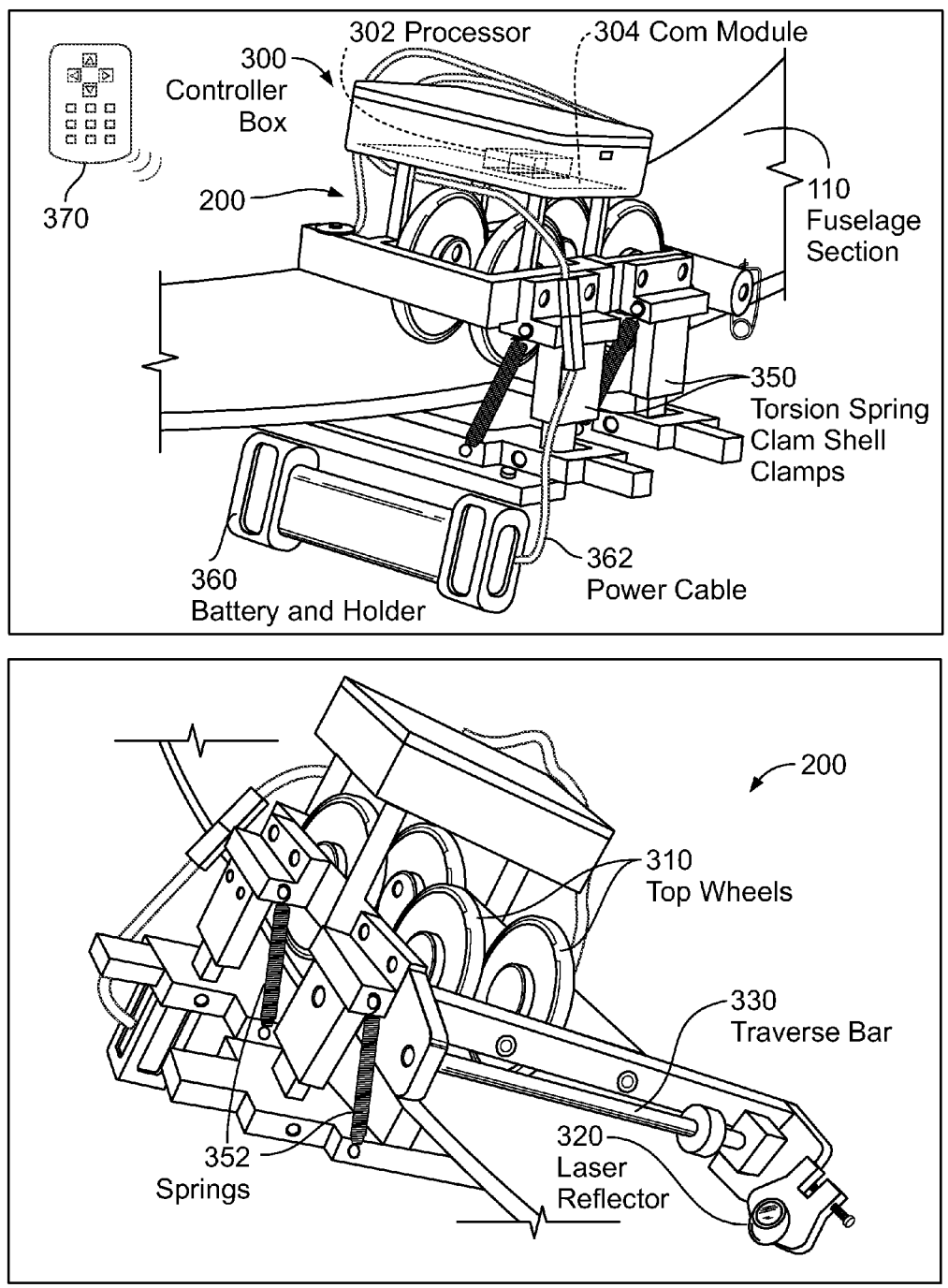
FIG. 3 is a diagram illustrating a circumferential laser crawler, in accordance with an advantageous embodiment of the invention.

FIG. 3 is a diagram illustrating a circumferential laser crawler, in accordance with an advantageous embodiment of the invention. Referring to FIG. 3, there is shown the crawler 200 of FIG. 2. Also shown in FIG. 3 is a user controller 370.

The crawler 200 may comprise a plurality of components that may perform and/or support various functions of the crawler 200. The crawler 200 may comprise, for example, a controller box 300, a plurality of wheels 310, a laser reflector 320, a traverse bar 330, one or more motors 340, one or more clamping assemblies 350, and a battery/holder assembly 360.

The controller box 300 may comprise suitable logic, circuitry, interfaces, and/or code for controlling operations and/or functions of the crawler 200, and/or components thereof. To that end, the controller box 300 may utilize internal connects to various components of the crawler 200, to enable interactions between these components and the controller box 300. The controller box 300 may comprise a processor 302, which may be operable to control and/or manage operations of the crawler 200. In this regard, the processor 302 may be operable to configure and/or control operations of various components and/or subsystems of the crawler 200, by utilizing control signals for example. The invention is not limited to any particular type of processors, and various types of processors may be used, including general purpose processors, microprocessors, and/or ASICs. The controller box 300 may also comprise a communication module 304, which may enable transmission and/or reception of data. In this regard, the communication module 304 may support wireless communications, in accordance with one or more wireless interfaces, technologies, and/or standards. For example, the communication module 304 may be configured to transmit and/or receive infra-red (IR) signals, Bluetooth signals, WiFi signals, and/or other similar type of signals.

The wheels 310 may be used to enable moving the crawler 200. In this regard, the motors 340 (shown in FIG. 4) may be utilized to provide automated motorized movement of the crawler 200, by driving at least some of moving components of the crawler 200, such as, such as one or more of the wheels 310. The motors 340 may be configured to provide continuous and/or constant rotation of the wheels 310. Movement of the crawler 200 may also comprise use of, beside the wheels 310, additional wheels and/or rollers, which may be in contact with other surfaces or edges—that is beside the surface on which the wheels 310 are running. In this regard, the additional wheels and/or rollers may support controlling the movement of the crawler 200, ensuring that the crawler 200 would remain tightly secured to the surfaces and/or edge during its movement. This enhanced quality of the movement of the crawler 200 may result in enhancing the reliability of the measurement performed based on that movement. The additional wheels and/or rollers need not be motorized—i.e., may not be driven by the motors 340. The invention, however, is not so limited and the motors 340 may be utilized to drive all moving components of the crawler 200.

To further enhance the movement of the crawler 200, a clamping mechanism may be utilized to further ensure that the various moving parts of the crawler 200 remain in contact with the surfaces and/or edges on which they run, and/or that the crawler 200 continually run as tightly as possible on the edge of the measured structure. For example, clamping assemblies 350 may be utilized to connect the wheels 310 to corresponding wheels running on the opposite surface of the fuselage section 110, and to push these wheels tightly into the fuselage section 110, thus pushing both of these wheels firmly against the surfaces on which they are running. Various mechanisms may be utilized to proving the clamping function. For example, a torsion spring, clam shell design may be utilized, in which springs 352 may be utilized to ensure that the wheels that are pressed into the surfaces on which they run, by pulling the different sets of wheels into each other.

The movement of the crawler 200 may be further enhanced by other means, to further ensure that the crawler 200 remain tightly secured to the surfaces and/or edge during its movement, and/to ensure that the position of the laser reflector 320 is maintained throughout the movement of the crawler 200. For example, some of the wheels and/or rollers may be grouped into separate sets, with these sets being configured to provide for rotational and/or lateral flexibility therebetween—i.e., the sets being able to be offset laterally (relative to the edge, thus conforming to any slanting in the edge) and/or rotationally (to better conform to the traversed surface while keeping the wheels and/or rollers in contact with the surface). This may be achieved by incorporating a tracking component for providing such lateral and/or rotational offsetting between the sets of wheels and/or rollers. These features are described in more details in one or more of the following drawings.

The laser reflector 320 may be operable to reflect laser beams, such as those emitted by the laser tracker 210. In this regard, the laser reflector 320 may be configured to optimally reflect signals generated and/or emitted by the laser tracker 210. A holding assembly may be utilized to hold the laser reflector 320. In this regard, the holding assembly of the laser reflector 320 may be utilized to attach the laser reflector 320 to the crawler 200, and may also be utilized to ensure that the laser reflector 320 remains in contact with the measured surface. Various mechanisms may be utilized to ensure that the laser reflector 320 may remain in contact with the traversed surface. For example, the laser reflector 320 may incorporate a spring-loaded design, in which the torsion springs may be utilized to push the laser reflector 320 tightly against the surface of the traversed surface (e.g., internal or external surfaces of the fuselage section 110). In some instances, the laser reflector 320 may be moved relative to the edge of the structure, to enable measuring different rows of data. This may be achieved by use of the traverse bar 330, which may enable sliding the holding assembly of the laser reflector 320 away and/or towards the edge. These features are explained in more detail in one or more of the following drawings.

The battery/holder assembly 360 may comprise one or more batteries for providing power to various components of the crawler 200, such as via one or more power cables 362, thus enabling operations thereof. In this regard, the battery/holder assembly 360 may comprise any type of battery that may be suitable to provide power to the crawler 200, and/or any components thereof. While the crawler 200 is described as having a battery based power supply, the invention is not so limited. Accordingly, any type of power supply that may be suitable for providing power to the crawler 200 may be utilized. In this regard, a power supply may be deemed suitable based on various considerations, including power related and non-power related factors. For example, power supply may be evaluated to determine if it may provide sufficient and/or suitable voltage or wattage, but may also be evaluated to determine whether it is of suitable size and/or weight—e.g., the power supply typically should not be too bulky or heavy as since excessive weight or size may adversely affect the movement of the crawler 200.

The user controller 370 may comprise suitable logic, circuitry, interfaces, and/or code for enabling users to interact with the crawler 200. In this regard, the user controller 370 may be utilized, for example, to send user input to the crawler 200, and/or to obtain information from the crawler 200. The user input may comprise, for example, commands pertaining to various functions or operations of the crawler 200. For example, the commands may comprise movement related commands, such as "start," "pause," and "stop;" and/or speed related commands (i.e., specifying particular speed for the movement of the crawler 200). The interactions between the user controller 370 and the crawler 200 may be performed via wireless communication. For example, the user controller 370 may be configured to transmit commands via infra-red (IR) signals, Bluetooth signals, WiFi signals, and/or other similar type of signals.

Figure 4:
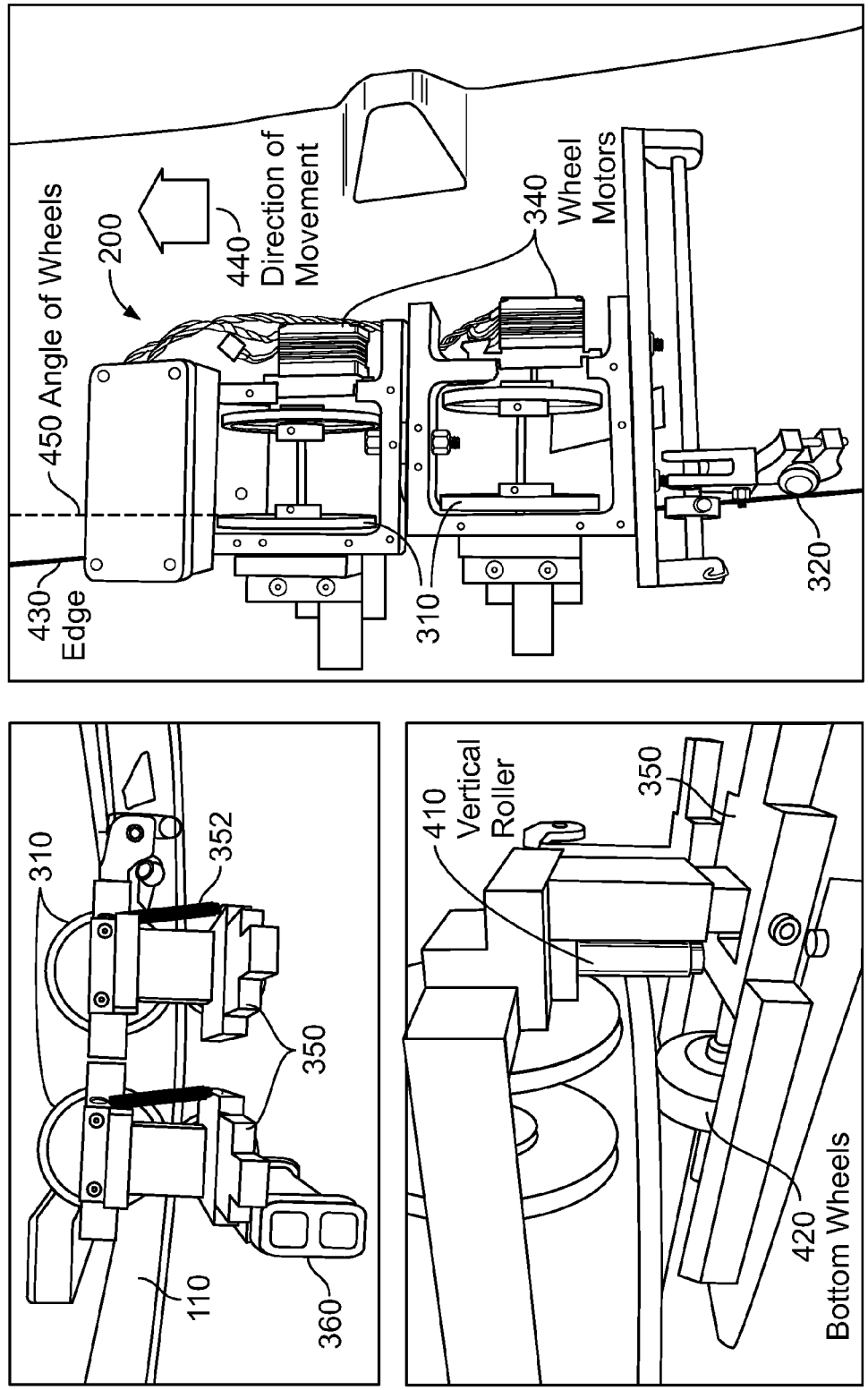
FIG. 4 is a diagram illustrating various moving and positioning components of a circumferential laser crawler, in accordance with an advantageous embodiment of the invention.

FIG. 4 is a diagram illustrating various moving and positioning components of a circumferential laser crawler, in accordance with an advantageous embodiment of the invention. Referring to FIG. 4, there is shown the crawler 200.

The crawler 200 may incorporate, in addition the wheels 310 described in FIG. 3, additional wheels and/or rollers that may ride along surfaces and/or edges other than the surfaces on which the wheels 310 are running, to enhance the movement of the crawler 200. For example, in addition to the top wheels 310, the crawler 200 may incorporate bottom wheels 420, which may move on the surface opposite of the surface on which wheels 310 are running; and/or vertical rollers 410, which may be contact with, and run on the edge of the structure whose circumferential data is being measured. It should be understood that the use of the terms "top" "bottom" and "vertical" is intended for explanatory and demonstrative purposes only, and that these terms do not impose spatial limitations with respect to the corresponding items. In other words, the "top" wheels are only top wheels in the sense that they are running on the top surface in the perspective of the crawler 200 shown in the drawings. The vertical rollers 410 may be utilized to ensure that the crawler 200 indexed (i.e., in tight contact) with the edge, and running on it. The use of bottom wheels, in addition to the top wheels, may make movement of the crawler easier.

To further enhance the movement of the crawler 200, a clamping mechanism may be utilized to further ensure that the various moving parts of the crawler 200 remain in contact with the surfaces and/or edges on which they run, and/or that the crawler 200 continually run as tightly as possible on the edge of the measured structure. For example, spring-torsion, clam shell clamping assemblies 350 may be utilized to connect the assemblies holding the top wheels 310 and the bottom wheels 420, thus pushing both of these wheels firmly against the surfaces on which they are running.

Another mechanism that may incorporated into the movement component of the crawler 200, to further ensure that the crawler 200 runs tightly along the edge 430 of the structure, is angling the wheels. In this regard, the top wheels 310 and/or bottom wheels 420 may be configured to move at an angled path 450, whereby the wheels may run slanted rather than straight, driving into the structure along the direction of movement 440 of the crawler 200 (as shown in in the top prospective view in FIG. 4), to further ensure that the crawler 200 remains tightly secured to the edge 430 of the structure as it moves along the edge 430. The use of vertical rollers 410 may assist the angled movement of the top wheels 310 and/or bottom wheels 410, by enabling the crawler 200 to run smoothly along the edge 430 while the angled movement of the wheels drives the crawler into the structure (and thus the edge 430).

Figure 5:
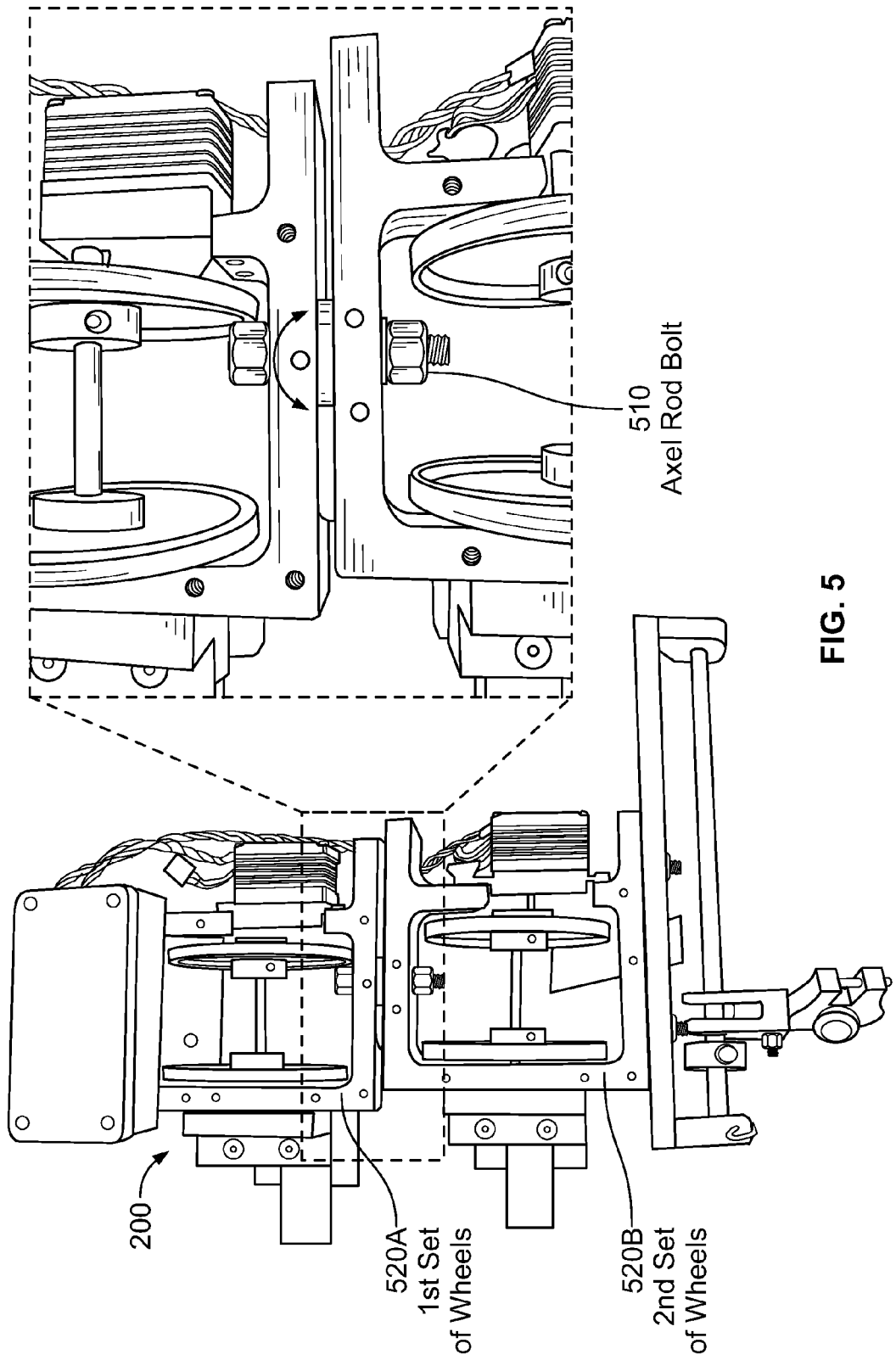
FIG. 5 is a diagram illustrating an articulated assembly of a circumferential laser crawler for enabling conforming to surfaces and/or for keeping moving components in contact with the surfaces, in accordance with an advantageous embodiment of the invention.

FIG. 5 is a diagram illustrating an articulated assembly of a circumferential laser crawler for enabling conforming to surfaces and/or for keeping moving components in contact with the surfaces, in accordance with an advantageous embodiment of the invention. Referring to FIG. 5, there is shown the crawler 200.

Another feature that may be incorporated into the crawler 200, to further ensure that the crawler 200 securely and tightly traverses curvilinear edges, including edges that may be uneven, is the grouping the moving parts (wheels and/or rollers) of the crawler 200 into separate sets. For example, some of the wheels of the crawler 200 may be grouped into separate assemblies, shown in FIG. 5 as a first set 520A and a second set 520B, with these sets being configured to allow for rotational and/or lateral adjustments relative to one another, to ensure that the crawler 200 may better conform to the edges and/or surfaces traversed. The first set 520A and the second set 520B may comprise any combination of moving parts of the crawler 200. For example, the first set 520A and the second set 520B may comprise only groups of top wheels 310, only groups of bottom wheels 420, and/or groups of both top wheels 310 and bottom wheels 420, and thus may also include a portion of the clamping component connecting the top and bottom wheels, and/or vertical roller(s).

The first set 520A and the second set 520B may be configured to incorporate an articulated assembly to allow these sets to rotate relative to each other, so that both sets (520A and 520B) may remain in contact, even when traversing a section with uneven surface, ensuring that most (or all) of the wheels remain in contact with the surface. In other words, incorporating the articulated assembly may enable the first set 520A and the second set 520B to independently tilt (right or left along the direction of movement 440), thus conforming to the surface areas that these sets are in contact with at any given point. This may be achieved, for example, by incorporating a single axle rod/bolt assembly 510 to connect the first set 520A and the second set 520B, thus allowing each to rotate, relative to each other, along an axle that is parallel to the direction of movement of the crawler 200. While the crawler 200 is shown with two sets (of wheels), the invention need not be so limited. Accordingly, different number of sets may be utilized, and/or with rotating assemblies being utilized to connect all or some of these sets as deemed optimal to achieve the best surface conformity characteristic for the crawler 200.

Figure 6:
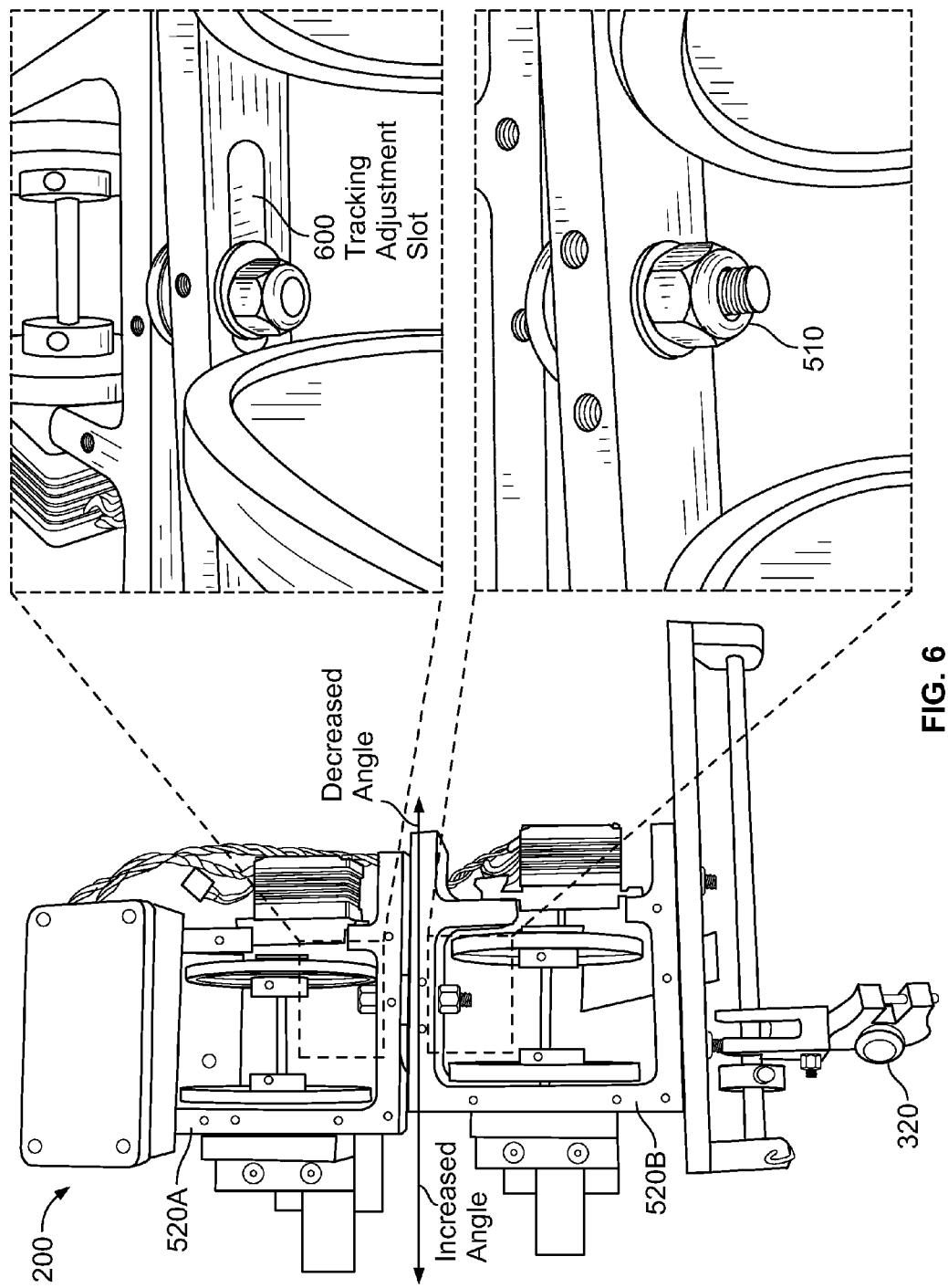
FIG. 6 is a diagram illustrating a tracking adjustment component of a circumferential laser crawler for enabling variable lateral adjustment of moving parts relative to edges, in accordance with an advantageous embodiment of the invention.

FIG. 6 is a diagram illustrating a tracking adjustment component of a circumferential laser crawler for enabling variable lateral adjustment of moving parts relative to edges, in accordance with an advantageous embodiment of the invention. Referring to FIG. 6, there is shown the crawler 200. Also, shown in FIG. 6 are the first set 520A and the second set 520B, which may be utilized when the crawler 200 may incorporated grouped based configuration of movement components.

The first set 520A and the second set 520B may be configured to incorporate a tracking adjustment, to allow these sets to move laterally relative to one another, so that both sets may independently try to remain in contact with the traversed edge, even when the edge is uneven—e.g., when the edge is slanted or angled. In this regard, allowing the first set 520A and the second set 520B to offset laterally may ensure that these sets may independently remain as tightly secured to the edge as possible, whereas not allowing such lateral offsetting may otherwise cause one of these sets to move away or dislodge from the edge. Therefore, incorporating tracking adjustment may enable the first set 520A and the second set 520B to independently remain in contact with to the edge even when the edge may not be straight. This may be achieved, for example, by incorporating a tracking adjustment slot 600 to enable any connection assembly connecting the two sets to move laterally. For example, the single axle rod/bolt assembly 510 utilized to connect the first set 520A and the second set 520B (allowing for rotational adjustment between the set) may be combined with the tracking adjustment slot 600, to also allow lateral offsetting, by enabling the axle rod/bolt assembly 510 to move within the tracking adjustment slot 600, thus allowing the sets to offset laterally such that the wheels in these sets may increase or decrease the amount the wheels drive away from the edge.

Figure 7:
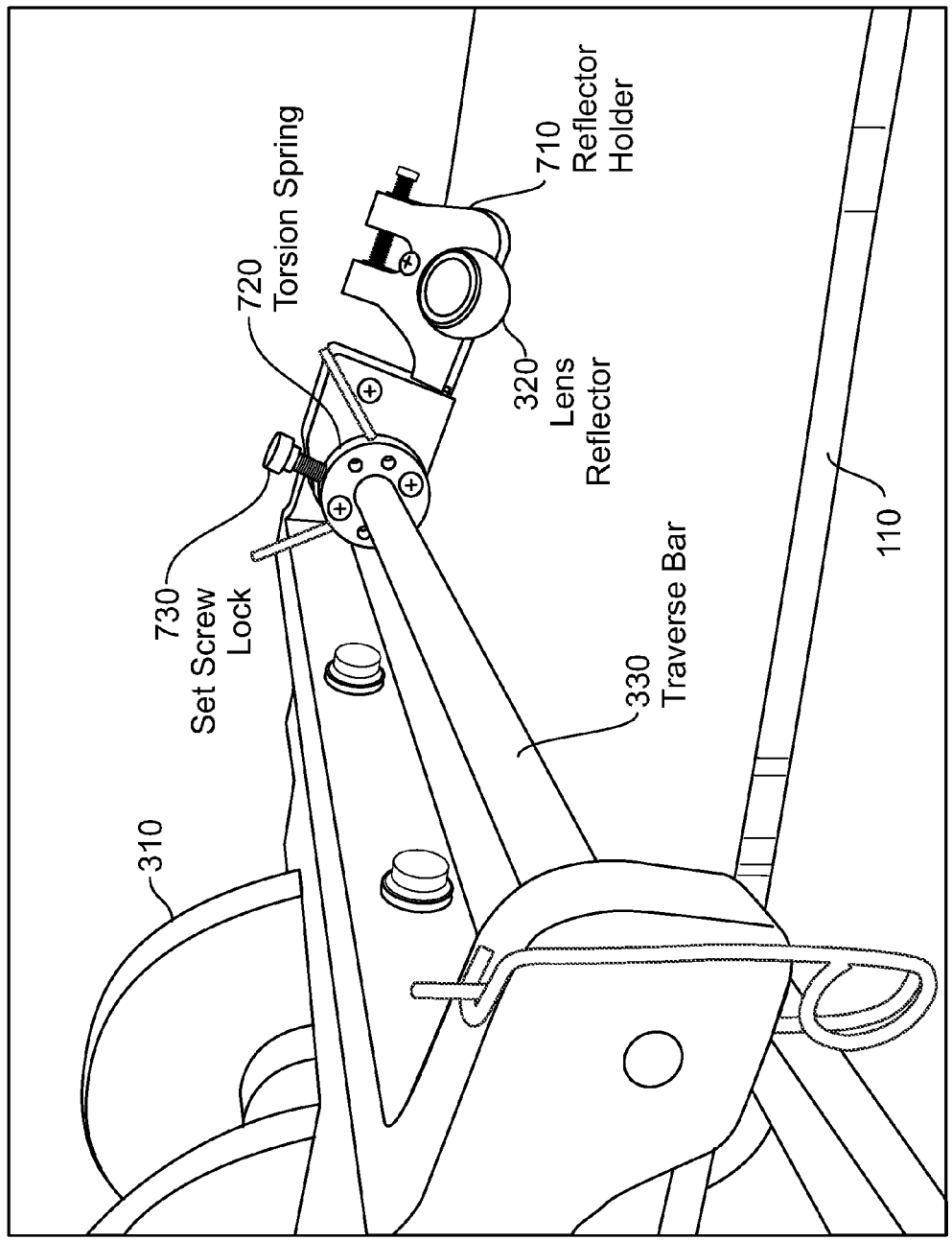
FIG. 7 is a diagram illustrating a reflector component of a circumferential laser crawler for enabling adjustment and locking of reflector relative to surfaces, in accordance with an advantageous embodiment of the invention.

FIG. 7 is a diagram illustrating a reflector component of a circumferential laser crawler for enabling adjustment and locking of reflector relative to surfaces, in accordance with an advantageous embodiment of the invention. Referring to FIG. 7, there is shown the laser reflector 320 of the crawler 200.

The laser reflector 320 may be attached to the crawler 200 to enable utilizing the laser tracker 210 in generating and/or obtaining measurement data pertaining to the structure whose edge is traversed by the crawler 200. A holding assembly may be utilized to hold the laser reflector 320, attach it to the crawler 200, and/or to maintain position of the laser reflector 320 relative to the surface of the structured being measured. In this regard, the reflector holder 710 may be utilized to hold the laser reflector 320 in position while the crawler 200 is moving. Because the laser reflector 320 may not be exactly on the surface being measured, the laser tracker 210 may be configured to account for any separation between the surface and the center of laser reflector 320 during the calculation performed in the course of obtaining and/or generating the measurement data. Various designs and/or mechanisms may be incorporated into the reflector holder 710 to ensure that the laser reflector 320 may remain in contact with the traversed surface, or maintain its position (e.g., when the laser reflector 320 is positioned off the surface, such as during measurements of external surfaces). For example, the laser reflector 320 may incorporate a spring-loaded design, in which the torsion spring 730 and the set screw lock 720 may be utilized to ensure that the laser reflector 320 remain in positions by use of spring loading force being applied against the locking mechanism. The torsion spring 730 may be utilized to apply torsion force on the reflector holder 710 to maintain contact (the holder and thus the reflector itself) with the surface. The set screw lock 720 may be utilized to lock the holding assembly in position. In some instances, the set screw lock 720 may be utilized to lock the holding assembly such that laser reflector 320 may be offset away from surface. This may be done, for example, when the crawler is setup to move along the edge such that the top part of the crawler corresponds to the outer surface of the structure, thus enabling generation of measurement data for the outside surface. In this regard, holding the laser reflector 320 at a distance from the surface may ensure that the laser reflector 320 remains seen by the laser tracker 210 as the crawler move along the edge of the structure (e.g., fuselage section 110). In such instances, the laser tracker 210 may be configured to account for that added distance from the surface during calculation performed in the course of obtaining and/or generating the measurement data.

The laser reflector 320 may be moved to different positions, on the surface of the structure (e.g., fuselage section 110) being measured, relative to the edge of the structure. Repositioning the laser reflector 320 may enable generating and/or obtaining plurality of circumferential rows of data. For example, the holding assembly—which may comprise the reflector holder 710, the set screw lock 720, and the torsion spring 730—may be configured to slide along the traverse bar 330 such that the laser reflector 320 may be positioned at different distances from the edge.

FIG. 8 is a diagram illustrating a reflector traversing component of a circumferential laser crawler for enabling adjustment of positioning of reflector relative to edges, in accordance with an advantageous embodiment of the invention. Referring to FIG. 8, there is shown the traverse bar 330 of the crawler 200.

The traverse bar 330 may be utilized to enable sliding the holding assembly, which holds the laser reflector 320, towards and/or away from the edge of the structure being measured, to enable generating plurality of circumferential rows of data. For example, the crawler 200 may initially be setup with the laser reflector 320 positioned at the near edge position 800, which may correspond to the closest position to the edge. After the crawler 200 completes a movement around the edge of the structure being measure, the laser reflector 320 may be reposition to each of multiple positions 810, up to the far edge position 820, which may correspond to the furthest position from the edge. The repositioning may be done by moving the holding assembly along the traverse bar 330. At each position the crawler 200 may complete a move along the edge, to generate corresponding circumferential measurement data, before being repositioned to the next position.

Figure 9:
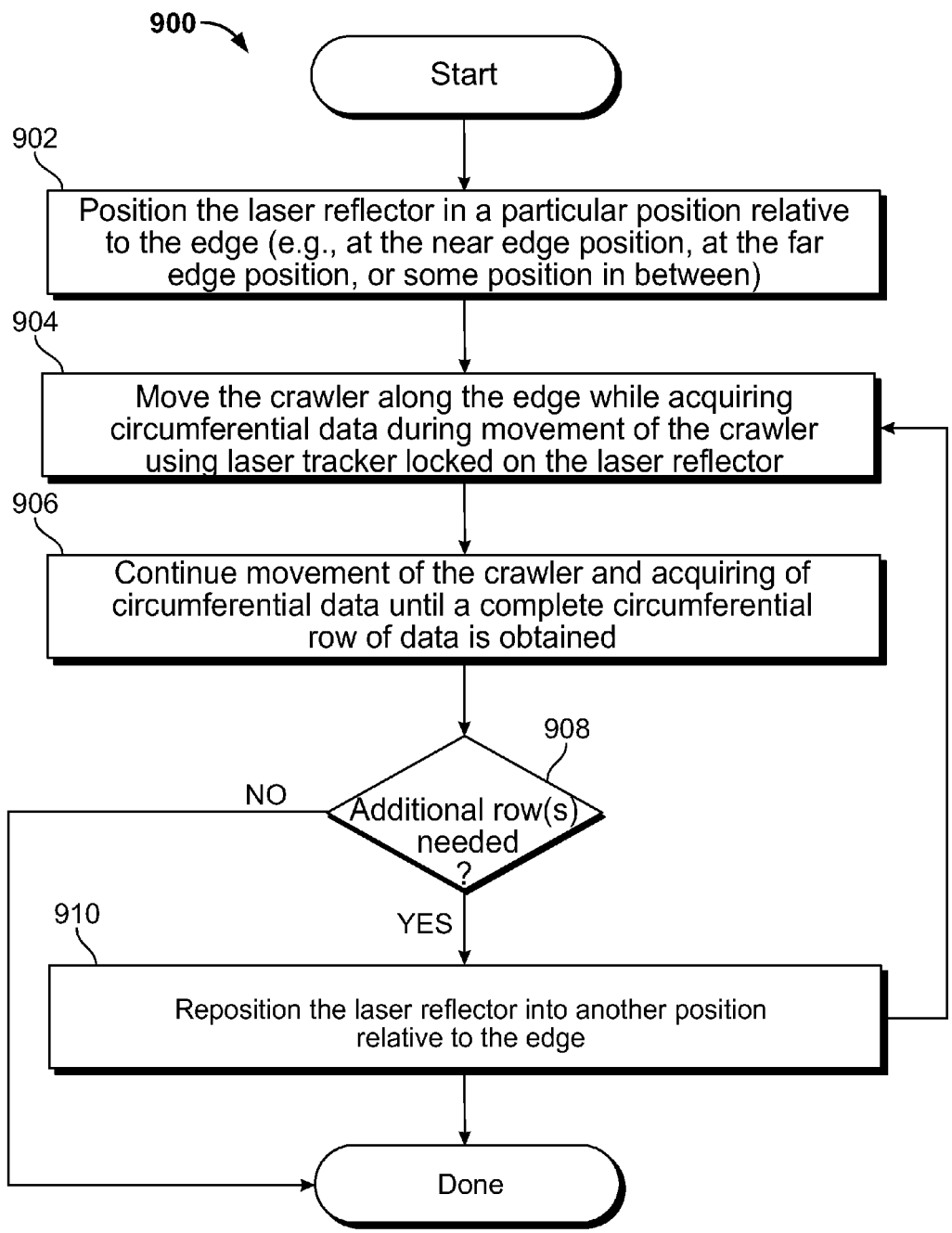
FIG. 9 is a flow chart that illustrates exemplary operations performed by a circumferential laser crawler during measurement, in accordance with an advantageous embodiment of the invention.

FIG. 9 is a flow chart that illustrates exemplary operations performed by a circumferential laser crawler during measurement, in accordance with an advantageous embodiment of the invention. Referring to FIG. 9, there is shown a flow chart 900 comprising a plurality of steps.

In step 902, a laser reflector may be positioned in a particular position relative to edge of a structure being measured. In this regard, the laser reflector may be attached to an automated motorized device (e.g., the laser reflector 320 of the crawler 200). In step 904, the crawler may move along the edge of the structure while circumferential coordinate data is being acquired during movement of the crawler, such as by use of laser tracker metrology system (e.g., laser tracker 210). In step 906, the movement of the crawler, and acquiring of circumferential data based thereon, may continue until a complete circumferential row of data is obtained and/or generated. In step 908, it may be determined whether additional circumferential rows of data are needed. If no additional circumferential row of data is needed, the plurality of steps may terminate.

Returning to step 908, if additional circumferential row of data is needed, the plurality of steps may proceed to step 910. In step 910, the laser reflector may be repositioned into another position relative to the edge. For example, after obtaining circumferential row of data corresponding to the near edge position 800, the laser reflector 320 may be repositions in one or more the multiple positions 810 and/or the far edge position 820. The plurality of step may then return to step 904, to enable obtaining and/or generating circumferential row of data corresponding to the new position.

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the steps as described herein for circumferential laser crawler.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other system adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. An apparatus, comprising:
an automated motorized device operable to run along a curvilinear shaped edge of a structure to acquire circumferential coordinate data, the automated motorized device comprising:
a movement component operable to move the automated motorized device along the curvilinear shaped edge of the structure, the movement component comprising a first roller mechanism and a second roller mechanism;
a clamping structure operable to movably secure the automated motorized device about the curvilinear shaped edge, the clamping structure comprising a first clamping arm, a second clamping arm, and an intermediate support coupled between the first clamping arm and the second clamping arm, wherein the first clamping arm operably supports the first roller mechanism in contact with a first side of the structure and the second clamping arm operably supports the second roller mechanism in contact with a second side of the structure, wherein the second side is opposite the first side, wherein the intermediate support engages the curvilinear shaped edge of the structure, the curvilinear shaped edge extending between the first side and second side of the structure; and
a reflector that is operable to reflect signals back to a source of the signals.

2. The apparatus of claim 1, wherein the reflector is spring loaded.

3. The apparatus of claim 1, wherein the automated motorized device comprises a sliding component for enabling movement of the reflector.

4. The apparatus of claim 1, wherein the clamping structure tightly secures the automated motorized device to the edge during movement of the automated motorized device along the edge.

5. The apparatus of claim 1, wherein the first and second roller mechanisms of the movement component compromise a plurality of wheels.

6. The apparatus of claim 5, wherein the plurality of wheels comprises one or more drive wheels that are driven by one or more motors in said automated motorized device.

7. The apparatus of claim 5, wherein the movement component further compromise a third roller mechanism and the intermediate support operably supports the third roller mechanism in contact with the edge of the structure.

8. The apparatus of claim 5, wherein the plurality of wheels comprises one or more wheels that drive at an angle relative to the edge and into the structure.

9. The apparatus of claim 5, wherein the automated motorized device comprises a tracking component for enabling at least some of the wheels to move independent of other wheels.

10. The apparatus of claim 1, wherein the automated motorized device comprises a controller for controlling operations of at least some of components of the automated motorized device.

11. The apparatus of claim 1, wherein the automated motorized device comprises a communication component for receiving and/or transmitting data, said data comprising user input, feedback and/or status information.

12. The apparatus of claim 11, wherein communication component is operable to communicate said data wirelessly to and/or from the automated motorized device.

13. A method, comprising:
  positioning a reflector of an automated motorized device in a particular position relative to a curvilinear edge of a structure; and
  obtaining circumferential row of data at the particular position by:
    moving the automated motorized device along the curvilinear edge, wherein the automated motorized device is movably clamped and wrapped around the curvilinear edge, wherein movement of the automated device is restricted by the curvilinear shaped edge;
    acquiring circumferential coordinate data during movement of the automated motorized device using a laser tracker metrology system; and
    continuing to move the automated motorized device and acquire circumferential data until a complete circumferential row of data is obtained.

14. The method of claim 13, wherein the structure is a fuselage section of an airplane.

15. The method of claim 13, comprising acquiring the circumferential coordinate data based on:
  transmitting of signals from the laser tracker metrology system, and
  receiving by the laser tracker metrology system signal reflections off of the reflector.

16. The method of claim 13, comprising obtaining a plurality of additional circumferential rows of data by:
  repositioning the reflector of the automated motorized device in a plurality of other positions, and
  obtaining a circumferential row of data at each of the plurality of other positions.

17. The method of claim 13, comprising communicating with the automated motorized device to send user input to the automated motorized device and/or to obtain information from the automated motorized device.

18. The method of claim 17, wherein the communicating with the automated motorized device is performed wirelessly.

19. The method of claim 17, wherein the user input is utilized to control at least some of operations of the automated motorized device.

* * * * *

UNITED STATES PATENT AND TRADEMARK OFFICE
CERTIFICATE OF CORRECTION

PATENT NO.        : 9,030,673 B2                                   Page 1 of 1
APPLICATION NO.   : 13/441239
DATED             : May 12, 2015
INVENTOR(S)       : Barry Theophile Cooke It is certified that error appears in the above-identified patent and that said Letters Patent is hereby corrected as shown below:

In the Claims

Column 14, Claim 7, line 52, third word, replace the word "compromise" with the word "comprises"

Signed and Sealed this
Twenty-fifth Day of August, 2015

Michelle K. Lee
*Director of the United States Patent and Trademark Office*